United States Patent [19]

Ishibe et al.

[11] Patent Number: 4,533,653

[45] Date of Patent: Aug. 6, 1985

[54] PREPARATION OF AN IMPROVED CATALYST FOR THE MANUFACTURE OF NAPHTHOQUINONE

[75] Inventors: Nobuyuki Ishibe; Renard L. Thomas, both of Lake Jackson; Emmett L. Tasset, Clute, all of Tex.

[73] Assignee: The Dow Chemical Company, Midland, Mich.

[21] Appl. No.: 451,123

[22] Filed: Dec. 20, 1982

[51] Int. Cl.³ .................. B01J 21/08; B01J 23/20
[52] U.S. Cl. .................................................. 502/242
[58] Field of Search ........................................ 502/242

[56] References Cited

U.S. PATENT DOCUMENTS

| | | |
|---|---|---|
| 1,844,387 | 2/1932 | Jaeger. |
| 2,698,306 | 12/1954 | Matejczyk ............................ 252/464 |
| 2,765,323 | 10/1956 | Dixon et al. ......................... 260/396 |
| 2,809,939 | 10/1957 | Dixon et al. ......................... 252/456 |
| 2,863,879 | 12/1958 | Tribit .................................. 260/346.4 |
| 2,863,884 | 12/1958 | Tribit et al. ......................... 260/396 |
| 3,012,043 | 12/1961 | Dowden et al. ..................... 260/346.4 |
| 3,095,430 | 6/1963 | Wettstein ............................ 260/396 |
| 3,232,955 | 2/1966 | Nonnenmacher et al. ........ 260/346.4 |
| 3,243,385 | 3/1966 | Sennewald et al. ............. 502/242 X |
| 3,402,187 | 9/1968 | Kaiser et al. ...................... 260/396 |
| 3,507,810 | 4/1970 | Sanborn et al. ................... 252/430 |
| 3,806,469 | 4/1974 | Morita et al. ...................... 252/432 |
| 3,897,464 | 7/1975 | Dohm et al. ..................... 260/346.4 |
| 4,032,548 | 6/1977 | Martin et al. .................... 260/396 R |
| 4,111,967 | 9/1978 | Martin et al. .................... 260/396 R |

FOREIGN PATENT DOCUMENTS

| | | | |
|---|---|---|---|
| 6133232 | 10/1981 | Japan | ........................... 502/242 |
| 882089 | 11/1961 | United Kingdom. | |

*Primary Examiner*—Carl F. Dees
*Attorney, Agent, or Firm*—A. C. Ancona

[57] ABSTRACT

An improved process of making an oxidation catalyst containing vanadium, tin, potassium and a silicate binder which comprises employing a porosity control agent and calcination conditions to produce a catalyst having a mean pore diameter in the range of 5–15$\mu$ and at least 90% of the pores having diameters $<10\mu$.

6 Claims, No Drawings

PREPARATION OF AN IMPROVED CATALYST FOR THE MANUFACTURE OF NAPHTHOQUINONE

BACKGROUND OF THE INVENTION

The oxidation of naphthalene can produce phthalic anhydride, naphthoquinone, $CO_2$ and $H_2O$. The present process is directed to a more selective production of the naphthoquinone, while minimizing the other by-products, such as phthalic anhydride.

The oxidation of naphthalene to make naphthoquinone is well known in the art. U.S. Pat. No. 1,844,387 issued in 1932 teaches the use of "non-silicious base exchange bodies" as catalysts for the vapor phase oxidation of naphthalene. The compounds useful for the catalysts are formed by reacting alkali metallates and metal salts. Salts of various metals, including copper, silver, beryllium, zinc, tin, lead, chromium, vanadium, iron, cobalt, platinum, palladium and the like, can be reacted with the metallates of many of the same metals, e.g. zinc, vanadium, tin, platinum and titanium.

U.S. Pat. No. 2,698,306 employs a catalyst for this oxidation process which consists of vanadium, tin and aluminum oxides with zirconium and titanium, optionally being employed in place of the tin. Tin oxide comprises from 50% up to 97% of the total weight of the catalyst. Other references employing vanadium oxides include U.S. Pat. Nos. 3,095,430; 3,402,187; 4,035,399 and 4,111,967. All of these also teach employing $K_2SO_4$; some employ carriers such as silica, pumice, corundum, and silicon carbide. The '430 patent and also the '387 and '306 patents teach tin as a component of such catalysts. The '430 patent also teaches the use of porosity controlling agents such as graphite and urea and the '187 patent adds naphthalene or oxalic acid for the same purpose.

SUMMARY OF THE INVENTION

The present invention is a catalyst of vanadium, usually present as $V_2O_5$, potassium, usually present as $K_2SO_4$ or $K_2S_2O_7$, and tin, usually present as the oxide $SnO_2$. Naphthalene or anthracene is preferably employed as the porosity controlling agent. Silicic acid is used as a binder or support for the catalytic components. The catalyst is useful in the oxidation of naphthalene to naphthoquinone.

DETAILED DESCRIPTION OF THE INVENTION

The catalyst was prepared by grinding in a ball mill the following compounds: ammonium vanadate, potassium sulfate, ammonium sulfate, stannic oxide, silicic acid, stearic acid and naphthalene. After thorough mixing, the finely ground components were compressed into a tablet and then calcined under a stream of air by gradually increasing the temperature over a period of several hours to 450° to 500° C. and maintaining that temperature for two hours. The air flow was discontinued for the final hour. After cooling the catalyst is ready for use.

The finished catalyst contains the metallic elements vanadium, tin and potassium. These are present as oxides or oxygen containing compounds, e.g. sulfates, pyrosulfates or vanadates. Thus, the tin or potassium may be present, at least in part, as the vanadate or the sulfates or pyrosulfates of the same elements may be present in the calcined catalyst. Part of the tin and vanadium may also be present as their oxides. Silica, which is employed as a binder, is added as silicic acid since the silica is in a hydrated form and readily soluble. The actual composition of the final catalyst is not known, but the proportions of the metals can be definitely stated.

The finished catalyst which is operable in the process for oxidizing naphthalene to naphthoquinone or anthracene to anthraquinone has the following proportions of metals $$V_a K_b Sn_c Si_d$$

wherein a is 1 to 5, b is 2.5 to 8.4, c is 4.3 to 8.6 and d is 2.6 to 5.2. A preferred ratio of the component elements is the catalyst wherein a is 1.8 to 3, b is 3.8 to 4.6, c is 5.2 to 6.3 and d is 3.1 to 3.8. Oxygen is present in sufficient amount to satisfy the valences of the metals present.

The calcination of the catalytic components is accomplished by heating in the presence of oxygen (not necessarily a flowing stream). Air is preferred. Temperatures of from about 400° to about 600° C. are required for a time of from about 2 to about 10 hours. Preferred temperature is in the range of from about 450° to about 550° C. for a preferred time of about 4 to about 8 hours.

The porosity of the catalyst is critical and, regardless of the porosity control agent, the conditions of preparation should produce a catalyst which has a mean pore diameter in the range of from about 5 to about 15$\mu$, preferably from about 7 to about 11$\mu$ and with at least about 90% of the pores having diameters of less than about 10$\mu$.

Representative catalysts had mean pore diameters and percentages of diameters $<10\mu$ according to Table I, following.

TABLE I

| Mean pore diam. ($\mu$) | % pores $<10\mu$ | Catalyst of Example |
|---|---|---|
| 7.23 | 94.4 | 7 |
| 8.71 | 94.5 | 1 |
| 10.12 | 92.6 | 17 |

With the above catalysts conversions of naphthalene were obtained of from about 9 to about 17% with selectivity to naphthoquinone of from about 70 to about 80%.

The following examples show the preparation of the catalyst and its use as an oxidation catalyst.

EXAMPLE 1

The following compounds were mixed together in a ball mill for six hours:

| | |
|---|---|
| $NH_4VO_3$ | 21 g |
| $K_2SO_4$ | 45 g |
| $(NH_4)_2SO_4$ | 13 g |
| $SnO_2$ | 35 g |
| Naphthalene | 37 g |
| Silicic acid | 21 g |
| Stearic acid | 3 g |

The mixture after thorough blending was compressed, using an extruding machine, into 3.5 mm cylindrical tablets 2.5 mm in diameter. The tablets were then calcined by heating in a stream of air (300 ml/min) and raising the temperature at the rate of 100° C./hr. to 500°

C., which temperature was maintained for two hours, the last hour without the flow of air.

Other catalysts were made in a similar manner. The amounts of components are shown in Table II.

TABLE II

| Example | Weight of Components (g) | | | | | | | |
|---|---|---|---|---|---|---|---|---|
| | $NH_4VO_3$ | $K_2SO_4$ | $(NH_4)_2SO_4$ | $SnO_2$ | $SiO_2 \cdot nH_2O$ | Naph. | $H_2WO_4$ | $Gd(NO_3)_3$ |
| *2 (comp.) | 21 | 45 | 13 | — | 21 | 37 | — | — |
| *3 (comp.) | 21 | 45 | 13 | 35 | 21 | — | — | — |
| 4 | 21 | 45 | 13 | 35 | 21 | 18.5** | — | — |
| 5 | 21 | 45 | 13 | 35 | 21 | 37 | 9.4 | — |
| 6 | 21 | 45 | 13 | 35 | 21 | 37 | — | 9.4 |
| 7 | 21 | 45 | 13 | 35 | 21 | 37 | — | — |

*Note that Examples 2 and 3 were comparative since they contained no tin and no porosity control agents, respectively.
**Anthracene was employed in Ex. 4.

The catalysts of the present invention are employed by passing vaporized naphthalene or anthracene along with oxygen or air over the catalyst at a space velocity of from about 2500 to about 5500 l/l/hr of air and from about 0.1 to about 0.5 g/g/hr of the hydrocarbon.

Temperatures of 300° to 500° C. are operable, but 350° to 450° C. are preferred.

EXAMPLE 8

The catalyst of Example 1 was employed to oxidize naphthalene by placing 25 g of the catalyst in a glass, tube 30 cm long×2 cm in diameter. The reactor was inserted into an electric tube furnace and heated to a temperature of 380° C. Naphthalene was preheated and vaporized before passing it into the reactor by means of a preheated stream of air (space velocity, 5294 1/l/hr). The space velocity of naphthalene was 0.13 g/g/hr. The pressure was atmospheric. The effluent from the reactor was condensed into a dry-ice cold trap and from thence passed through a methylene chloride scrubber to condense volatile products. Analysis of the product mixture by gas chromatography showed a 9% conversion of the naphthalene and a selectivity to 1,4 naphthoquinone of 75%. The remaining catalysts were also likewise employed. The conditions and results are shown in Table III.

TABLE III

| Example No. | Catalyst Example | Temp. (°C.) | Press. (psia) | Space Velocity | | Conv. (%) | Selec* (%) |
|---|---|---|---|---|---|---|---|
| | | | | Air (l/l/hr) | Naphth. (g/g/hr) | | |
| 9 | 2 (Comp.) | 400 | 14.7 | 3463 | 0.26 | 13 | 44 |
| 10 | 3 (Comp.) | 400 | 14.7 | 3529 | 0.13 | 24 | 31 |
| 11 | 4 | 400 | 14.7 | 3529 | 0.38 | 11 | 60 |
| 12 | 5 | 390 | 14.7 | 3000 | 0.25 | 18 | 64 |
| 13 | 6 | 390 | 14.7 | 3035 | 0.18 | 48 | 44 |
| 14 | 7 | 400 | 14.7 | 3405 | 0.18 | 18 | 69 |

*to naphthoquinone based on naphthalene converted

EXAMPLE 15

The composition of the catalyst in Example 1 was used to make a catalyst but the mixture was calcined at 450° C. for 16 hours using an air flow of 300 ml/min. This catalyst was employed to oxidize naphthalene at an air flow of 10570 l/l/hr, a naphthalene space velocity of 0.31 g/g/hr, temperature of 380° C. and atmospheric pressure. The conversion obtained was 18% and selectivity 62% to naphthoquinone.

EXAMPLE 16

The catalyst of Example 1 was employed as in Example 7 but under the following conditions:

| Example | Temp. (°C.) | Pres. (psia) | Space Vel. | | Conv. (%) | Selec. (%) |
|---|---|---|---|---|---|---|
| | | | Air (l/l/hr) | Naphth. (g/g/hr) | | |
| 14(a) | 380 | 39 | 2000 | 0.13 | 16 | 76 |
| 14(b) | 400 | 14.7 | 2824 | 0.37 | 22 | 71 |

EXAMPLE 17

The catalyst mixture employed in Example 1 was calcined at 500° C. for 4 hours using an air flow of 300 ml/min and then heated an additional hour in the absence of the air flow.

This catalyst was employed in a reactor at 400° C. at atmospheric pressure, a space velocity of 3529 l/l/hr (air), 0.14 g/g/hr (naphth.). The result was a conversion of 19% and a selectivity of 73% to naphthoquinone.

Using the catalyst of Example 1, anthracene was oxidized to anthraquinone. The temperature of the reactor was 415° C., the space velocity of air was 4235 l/l/hr and of anthracene 0.23 g/g/hr. The conversion obtained was 97% and selectivity was 98% to anthraquinone.

We claim:

1. In the process of making an oxidation catalyst containing vanadium, tin and potassium with a silicate binder the improvement which comprises employing an organic porosity control agent consisting of naphthalene, anthracene or a mixture thereof during the catalyst preparation to produce a catalyst having a mean pore diameter of from about 5 to about 15 microns and wherein at least 90% of the pores have diameters of less than about 10 microns.

2. A process of making a catalyst for the vapor phase oxidation of naphthalene or anthracene to produce naphthoquinone and anthraquinone, respectively, which comprises (1) combining ammonium vanadate, potassium sulfate, ammonium sulfate, tin oxide, silicic acid and an organic porosity control agent consisting of naphthalene, anthracene or a mixture thereof, (2) thoroughly grinding and mixing these components, (3) compressing said mixture into tablets and (4) calcining said tablets at a temperature of from about 400° to about 600°

C., whereby a catalyst is produced having a mean pore diameter of from about 5 to about 15 microns and wherein at least 90% of the pores have diameters of less than about 10 microns.

3. The process of claim 2 wherein the amounts of vanadium, potassium, tin and silicon compounds are sufficient to produce a finished catalyst having a metal atomic ratio of $$V_{1-5}K_{2.5-8.4}Sn_{4.3-8.6}Si_{2.6-5.2}$$

and wherein oxygen is present in an amount to satisfy the valences of the metal atoms present.

4. The process of claim 3 wherein the calcining is conducted at a temperature of from about 450° to about 550° C.

5. The process of claim 4 wherein the calcining is conducted for a period of from about 4 to about 8 hours.

6. The process of claim 5 wherein the atomic ratio of metals in the finished catalyst is $$V_{1.8-3}K_{3.8-4.6}Sn_{5.2-6.3}Si_{3.1-3.8}.$$

* * * * *